US008821925B2

(12) United States Patent
Fantuzzi

(10) Patent No.: US 8,821,925 B2
(45) Date of Patent: Sep. 2, 2014

(54) UBIQUINOL AND ALPHA LIPOIC ACID COMPOSITIONS

(71) Applicant: Soft Gel Technologies, Inc., Los Angeles, CA (US)

(72) Inventor: Michael Fantuzzi, Glendale, CA (US)

(73) Assignee: Soft Gel Technologies, Inc., Los Angeles, CA (US)

(*) Notice: Subject to any disclaimer, the term of this patent is extended or adjusted under 35 U.S.C. 154(b) by 0 days.

(21) Appl. No.: 13/731,559

(22) Filed: Dec. 31, 2012

(65) Prior Publication Data

US 2013/0129821 A1    May 23, 2013

Related U.S. Application Data

(62) Division of application No. 12/048,350, filed on Mar. 14, 2008, now Pat. No. 8,343,541.

(60) Provisional application No. 60/895,057, filed on Mar. 15, 2007, provisional application No. 60/908,477, filed on Mar. 28, 2007, provisional application No. 60/977,234, filed on Oct. 3, 2007.

(51) Int. Cl.
*A61K 9/64* (2006.01)
*A61K 38/43* (2006.01)
*C07C 45/00* (2006.01)

(52) U.S. Cl.
USPC ............... 424/456; 424/94.1; 568/309

(58) Field of Classification Search
USPC .................. 424/456, 94.1; 568/309
See application file for complete search history.

(56) References Cited

U.S. PATENT DOCUMENTS

| | | |
|---|---|---|
| 4,029,760 A | 6/1977 | De Roeck born Holtzhauer |
| 4,343,816 A | 8/1982 | Cavazza |
| 4,559,222 A | 12/1985 | Enscore et al. |
| 4,565,700 A | 1/1986 | Suzuki |
| 4,599,232 A | 7/1986 | Bertelli |
| 4,687,782 A | 8/1987 | Brantman |
| 4,824,669 A | 4/1989 | Folkers et al. |
| 4,840,970 A | 6/1989 | Ohasi et al. |
| 5,030,458 A | 7/1991 | Shug et al. |
| 5,240,961 A | 8/1993 | Shug |
| 5,290,605 A | 3/1994 | Shapira |
| 5,298,246 A | 3/1994 | Yano et al. |
| 5,310,578 A | 5/1994 | Thurn-Muller et al. |
| 5,362,753 A | 11/1994 | Blum et al. |
| 5,378,461 A | 1/1995 | Neigut |
| 5,391,550 A | 2/1995 | Carniglia et al. |
| 5,431,916 A | 7/1995 | White |
| 5,500,416 A | 3/1996 | Miyazawa et al. |
| 5,504,072 A | 4/1996 | Schmidl et al. |
| 5,512,691 A | 4/1996 | Barnicki et al. |
| 5,532,002 A | 7/1996 | Story |
| 5,552,167 A | 9/1996 | Taylor et al. |
| 5,560,928 A | 10/1996 | Defelice |
| 5,591,772 A | 1/1997 | Lane et al. |
| 5,626,849 A | 5/1997 | Hastings et al. |
| 5,637,316 A | 6/1997 | Ribier et al. |
| 5,645,856 A | 7/1997 | Lacy et al. |
| 5,670,320 A | 9/1997 | Wallace et al. |
| 5,686,491 A | 11/1997 | Sherwood |
| 5,716,928 A | 2/1998 | Benet et al. |
| 5,756,291 A | 5/1998 | Griffin |
| 5,843,476 A | 12/1998 | Ribier et al. |
| 5,858,401 A | 1/1999 | Bhalani et al. |
| 5,889,062 A | 3/1999 | Hoppe et al. |
| 5,891,469 A | 4/1999 | Amselem |
| 5,912,272 A | 6/1999 | Hoppe et al. |
| 5,916,591 A | 6/1999 | Bierdel-Willkommen |
| 5,948,443 A | 9/1999 | Riley et al. |
| 5,968,987 A | 10/1999 | Charman et al. |
| 5,976,568 A | 11/1999 | Riley |
| 5,977,162 A | 11/1999 | Seidman |
| 5,980,939 A | 11/1999 | Kim et al. |
| 5,985,344 A | 11/1999 | Cherukuri et al. |
| 6,008,192 A | 12/1999 | Al-Razzak et al. |
| 6,020,383 A | 2/2000 | Stone et al. |
| 6,033,678 A | 3/2000 | Lorenzen |
| 6,048,846 A | 4/2000 | Cochran |
| 6,048,886 A | 4/2000 | Neigut |
| 6,054,136 A | 4/2000 | Farah et al. |
| 6,056,971 A | 5/2000 | Goldman |
| 6,063,432 A | 5/2000 | Maxwell et al. |
| 6,069,167 A | 5/2000 | Sokol |
| 6,080,788 A | 6/2000 | Sole et al. |
| 6,096,338 A | 8/2000 | Lacy et al. |

(Continued)

FOREIGN PATENT DOCUMENTS

| | | |
|---|---|---|
| DE | 3512054 | 10/1986 |
| EP | 0 882 450 | 1/1998 |

(Continued)

OTHER PUBLICATIONS

Anderson Provisional U.S. Appl. No. 60/253,874, David M. Anderson, Applicant, filed Nov. 29, 2000, 21 pages.
Al-Hasso, Shahla, "Coenzyme Q10: A Review," *Hospital Pharmacy*, vol. 36, No. 1, pp. 51-55, 2000 Facts and Comparisons.
Author Unknown, "pformulate: A Soft Gell!!" 2000, pp. 1-6, found at URL: http://www.pformulate.com/pformsoftgel.htm.
Author Unknown, Paul Karrer Biography, Nobel Prizes, Nobel Prize in Chemistry, nobelprize.org, printed on Jan. 5, 2007, 2 pages.
Author Unknown, Oilseeds International Ltd., Rice bran oil- a health benefit, http://www.oilseedssf.com/products/prod.rice.html, 2002, printed on Mar. 6, 2006; 2 pages.
Bhandari, et al., "Preparation, Characterization and Evaluation of Coenzyme Q10 Binary Solid Dispersions for Enhanced Solubility and Dissolution," *Biol Pharm. Bull.*, 2007, vol. 30, No. 6, pp. 1171-1176.

(Continued)

*Primary Examiner* — Brian-Yong Kwon
*Assistant Examiner* — Jennifer A Berrios
(74) *Attorney, Agent, or Firm* — Winthrop & Weinstine, P.A.

(57) ABSTRACT

The present invention is directed to compositions and methods of delivery of CoQ that is reduced in the presence of lipoic acid and, optionally a fatty acid and/or optionally in a monoterpene. The compositions that include the reduced CoQ can be formulated in soft gel capsules.

18 Claims, No Drawings

(56) References Cited

U.S. PATENT DOCUMENTS

| | | | |
|---|---|---|---|
| 6,121,234 A | 9/2000 | Benet et al. |
| 6,174,547 B1 | 1/2001 | Dong et al. |
| 6,184,255 B1 | 2/2001 | Mae et al. |
| 6,197,349 B1 | 3/2001 | Westesen et al. |
| 6,200,550 B1 | 3/2001 | Masterson et al. |
| 6,203,818 B1 | 3/2001 | Vester |
| 6,207,137 B1 | 3/2001 | Shuch et al. |
| 6,218,436 B1 | 4/2001 | Howard et al. |
| 6,232,346 B1 | 5/2001 | Sole et al. |
| 6,261,575 B1 | 7/2001 | Hoppe et al. |
| 6,267,985 B1 | 7/2001 | Chen et al. |
| 6,277,431 B1 | 8/2001 | Berry et al. |
| 6,284,268 B1 | 9/2001 | Mishra et al. |
| 6,300,361 B1 | 10/2001 | Vivilecchia et al. |
| 6,300,377 B1 | 10/2001 | Chopra |
| 6,335,361 B1 | 1/2002 | Hamilton |
| 6,342,526 B1 | 1/2002 | Vervuert et al. |
| 6,365,181 B1 | 4/2002 | Matthews |
| 6,368,618 B1 | 4/2002 | Jun et al. |
| 6,426,362 B1 | 7/2002 | Miller et al. |
| 6,428,779 B1 | 8/2002 | Sauermann et al. |
| 6,436,431 B1 | 8/2002 | Hoffpauer et al. |
| 6,441,050 B1 | 8/2002 | Chopra |
| 6,455,589 B1 | 9/2002 | Ames et al. |
| 6,469,024 B2 | 10/2002 | Tino et al. |
| 6,472,378 B2 | 10/2002 | von Borstel |
| 6,479,069 B1 | 11/2002 | Hamilton |
| 6,503,483 B2 | 1/2003 | Shuch et al. |
| 6,503,506 B1 | 1/2003 | Germano |
| 6,503,523 B2 | 1/2003 | Hoppe et al. |
| 6,506,915 B1 | 1/2003 | West |
| 6,528,042 B1 | 3/2003 | Brown et al. |
| 6,545,184 B1 | 4/2003 | Lipshutz |
| 6,552,004 B1 | 4/2003 | Elazhary et al. |
| 6,562,869 B1 | 5/2003 | Hamilton et al. |
| 6,569,463 B2 | 5/2003 | Patel et al. |
| 6,579,854 B1 | 6/2003 | Mitchell et al. |
| 6,616,942 B1 | 9/2003 | Udell |
| 6,623,734 B2 | 9/2003 | Udell et al. |
| 6,630,170 B2 | 10/2003 | Balkus et al. |
| 6,664,287 B2 | 12/2003 | Avery et al. |
| 6,730,319 B2 | 5/2004 | Maeder et al. |
| 6,740,338 B1 | 5/2004 | Chopra |
| 6,782,307 B2 | 8/2004 | Wilmott et al. |
| 6,790,465 B2 | 9/2004 | Weissman |
| 6,806,259 B2 | 10/2004 | Udell et al. |
| 6,855,733 B2 | 2/2005 | Udell et al. |
| 6,955,820 B1 | 10/2005 | Udell |
| 7,015,245 B2 | 3/2006 | Rich et al. |
| 7,026,361 B2 | 4/2006 | Minemura et al. |
| 7,060,263 B2 | 6/2006 | Udell et al. |
| 7,169,385 B2 | 1/2007 | Fantuzzi et al. |
| 7,182,950 B2 | 2/2007 | Garti et al. |
| 7,220,429 B2 | 5/2007 | Udell |
| 7,273,606 B2 | 9/2007 | Fantuzzi et al. |
| 7,273,622 B2 | 9/2007 | Udell et al. |
| 7,588,786 B2 | 9/2009 | Khan et al. |
| 7,713,523 B2 | 5/2010 | Fantuzzi et al. |
| 7,815,943 B2 | 10/2010 | Hennen |
| 8,097,279 B2 | 1/2012 | Hassan et al. |
| 8,105,583 B2 | 1/2012 | Fantuzzi |
| 8,124,072 B2 | 2/2012 | Fantuzzi |
| 8,147,826 B2 | 4/2012 | Fantuzzi |
| 8,343,541 B2 | 1/2013 | Fantuzzi |
| 2002/0098172 A1 | 7/2002 | Udell et al. |
| 2003/0082168 A1 | 5/2003 | Yegorova |
| 2003/0108600 A1 | 6/2003 | Okibayashi et al. |
| 2003/0147927 A1 | 8/2003 | Khan et al. |
| 2003/0176500 A1 | 9/2003 | Molly et al. |
| 2003/0232076 A1 | 12/2003 | Makino et al. |
| 2004/0001874 A1 | 1/2004 | Davidson et al. |
| 2004/0047922 A1 | 3/2004 | Elstner |
| 2004/0166157 A1 | 8/2004 | Thombre |
| 2005/0025756 A1 | 2/2005 | Erwin |
| 2005/0031681 A1 | 2/2005 | Udell et al. |
| 2005/0036998 A1 | 2/2005 | Udell |
| 2005/0037066 A1 | 2/2005 | Udell et al. |
| 2007/0269508 A1 | 11/2007 | Udel |
| 2008/0003279 A1 | 1/2008 | Udell |
| 2008/0020022 A1 | 1/2008 | Udell |
| 2008/0089877 A1 | 4/2008 | Udell et al. |
| 2008/0226710 A1 | 9/2008 | Fantuzzi |
| 2012/0121566 A1 | 5/2012 | Fantuzzi |
| 2012/0153519 A1 | 6/2012 | Fantuzzi |

FOREIGN PATENT DOCUMENTS

| | | |
|---|---|---|
| EP | 0 888 774 | 1/1999 |
| EP | 1 728 506 | 3/2006 |
| JP | 55081813 | 6/1980 |
| JP | S57042616 | 3/1982 |
| JP | 5770815 | 5/1982 |
| JP | S57142911 | 9/1982 |
| JP | 59172417 | 9/1984 |
| WO | WO 88/03015 | 5/1988 |
| WO | WO 98/40086 | 9/1998 |
| WO | WO 98/56368 | 12/1998 |
| WO | WO 00/51574 | 9/2000 |
| WO | WO 01/52822 | 7/2001 |
| WO | WO 02/09685 | 2/2002 |
| WO | WO 03/105607 | 12/2003 |
| WO | WO 2004/066925 | 8/2004 |
| WO | WO 2005/032278 | 4/2005 |
| WO | WO 2005/089740 | 9/2005 |
| WO | WO 2005/092123 | 10/2005 |

OTHER PUBLICATIONS

Bliznakov, et al., "Biochemical and Clinical Consequencs of Inhibiting Coenzyme Q10 Biosynthesis by Lipid-Lowering HMG-CoA Reductase Inhibitors (Statins): A Critical Overview," *Advances in Therapy*, Jul./Aug. 1998, vol. 15, No. 4, pp. 218-228.

Chopra, et al., "Relative Bioavailability of Coenzyme Q10 Formulations in Human Subjects," *Internat. J. Vit. Nutr. Res.*, 1998, vol. 68, pp. 109-113.

Chopra, et al., "A New Coenzyme Q10 Preparation with Enhanced Bioavailability," *FASEB Journal*, 1997, vol. 11, No. 3, pp. A586 (Abstract).

Comax Q10 Trademark Registration Abstract and Specimen, Registration No. 1764014, registered Apr. 13, 1993, 26 pages.

Constantinescu, et al., "A Randomized Study of the Bioavailability of Different Formulations of Coenzyme Q10 (Ubiquinon)," The Journal of Clinical Pharmacology, 2007; 47: 1580-1586.

CRC Handbook of Chemistry and Physics, 51st Edition, R.C. Weast (Editor), The Chemical Rubber Co., Cleveland, Ohio, 1970, pp. C-309, 356, 364, 392, 434 and 488.

Density of Cooking Oil, *The Physics Factbook*, edited by Glenn Elert, dated unknown, 3 pages.

Dictionary.com accessed on Jan. 17, 2007, "thixotropic" 1 page.

Grant & Hackh's Chemical Dictionary, Definition of Gelatin, Fifth Edition, McGraw-Hill Book Company, 1987, p. 258.

Greenberg, et al., "Co-enzyme Q10: a new drug for cardiovascular disease," *The Journal of Clinical Pharmacology*, 1990, vol. 30, pp. 596-608.

Kang et al., "Physicochemical studies of lidocaine-menthol binary systems for enhanced membrane transport," *International Journal of Pharmaceutics*, 206 (2000) 35-42.

Kaplun-Frischoff, et al., "Testosterone Skin Permeation Enhancement by Menthol through Formation of Eutectic with Drug and Interaction with Skin Lipids," Journal of Pharmaceutical Sciences, vol. 86, No. 12, Dec. 1997, pp. 1394-1399.

Kommuru, et al., "A simplified chromatographic method for quantitative determination of coenzyme Q10 in dog plasma," *Journal of Pharmaceutical and Biomedical Analysis*, 16 (1998) 1037-1040.

Kommuru, et al., "Racemate and Enantiomers of Ketoprofen: Phase Diagram, Thermodynamic Studies, Skin Permeability, and Use of Chiral Permeation Enhancers," *Journal of Pharmaceutical Sciences* vol. 87, No. 7, Jul. 1998, pp. 833-840.

(56) References Cited

OTHER PUBLICATIONS

Kommuru, et al., "Self-emulsifying drug delivery systems (SEDDS) of coenzyme Q10: formulation development and bioavailabiilty assessment," *International Journal of Pharmaceutics*, 2001, vol. 212, pp. 233-246.

Merriam-Webster Dictionary OnLine, definition of "elixir," http://www.merriamwebster.com/dictionary/elixir, printed from the Jun. 3, 2009, 2 pages.

Nazzal et al., "Preparation and in vitro characterization of a eutectic based semisolid self-nanoemulsified drug delivery system (SNEDDS) of ubiquinone: mechanism and progress of emulsion formation," *International Journal of Pharmaceutics* 235 (2002) 247-265.

Nazzal et al., "Response Surface Methodology for the Optimization of Ubiquinone Self-Nonoemulsified Drug Delivery System," *AAPSPharmSciTech* 2002; 3 (1) article 3, pp. 1-9, Published: Feb. 8, 2002, found at URL: http://www.aapspharmscitech.org.

Padilla-Zakour, "Chemical Food Preservatives: Bonzoate and sorbate," *Venture*, New York State Agriculture Experimental Station, 1998, vol. 1, No. 2, 3 pages, found at URL: http://www.nysaes.cornell.edu/necfe/pubs/pdf/Venture/venture2_chemical.html.

Palamakula, et al., "Preparation and in Vitro Characterization of SelfNanoemulsified Drug Delivery Systems of Coenzyme Q10 Using Chiral Essential Oil Components," Pharmaceutical Technology, Oct. 2004, pp. 74-88.

Pouton, Colin W., "Lipid formulations for oral administration of drugs: non-emulsifying, self-emulsifying and 'self-microemulsifying' drug delivery systems," *European Journal of Pharmaceutical Sciences* 11 Suppl. 2 (2000) S93-S98.

RITO Partnership, Rice Bran Oil Info, http://web.archive.org/web/20020809203831/http://www.ricebranoil.info/why/index.html, web page of Aug. 9, 2002, printed from the Internet on Apr. 29, 2009, 1 page.

Shojaei et al., "Transbuccal permeation of a nucleoside analog, dideoxycytidine: effects of menthol as a permeation enhancer," *International Journal of Pharmaceutics* 192 (1999) 139-146.

Shrestha et al., "Aqueous Phase Behavior of Diglycerol Fatty Acid Esters," *Journal of Dispersion Science and Technology*, 28: pp. 883-891, 2007.

Siekmann et al., "Preparation and Physicochemical Characterization of Aqueous Dispersions of Coenzyme Q10 Nanoparticles," Pharmaceutical Research, vol. 12, No. 2, 1995.

Walker, "Mass, Weight, Density or Specific Gravity of Liquids, Specific Gravity of Liquids," 2007, SImetric.co.uk [http://www.simetric.co.uk/si_liquids.htm], 5 pages.

Weber, et al., "Intestinal Absorption of Coenzyme Q10 Administered in a Meal or as Capsules to Healthy Subjects," *Nutrition Research*, vol. 17, No. 6, pp. 941-945, 1997.

Weis, et al., "Bioavailability of Four Oral Coenzyme Q10 Formulations in Health Volunteers," *Molec. Aspects. Med.*, 1994, vol. 15, Supplement, pp. s273-s280.

Third Party Requestor's Comments under 35 C.F.R. 314(B)(2) and 37 C.F.R. 1.947 in Inter Partes Reexamination of U.S. Patent No. 8,124,072, Feb. 22, 2013, 74 pages.

Third Party Requestor's Comments under 35 C.F.R. 314(B)(2) and 37 C.F.R. 1.947 in Inter Partes Reexamination of U.S. Patent No. 8,105,583, Feb. 22, 2013, 52 pages.

Third Party Requestor's Comments under 35 C.F.R. 314(B)(2) and 37 C.F.R. 1.947 in Inter Partes Reexamination of U.S. Patent No. 8,147,826, Feb. 22, 2013, 33 pages.

Order Construing Claims and Granting Defendants' Motion for Summary Judgment entered Aug. 2, 2012, CV 10-0301 PSG (JCx), *Jarrow Formulas, Inc.* v. *Now Health Group, Inc.*, 28 pages.

Amendment filed Jan. 15, 2008, to Office Action dated Sep. 17, 2007, U.S. Appl. No. 10/293,932, 16 pages.

Amendment filed Mar. 11, 2009, to Office Action dated Sep. 11, 2008, U.S. Appl. No. 10/293,932, 16 pages.

Office Action (Restriction Requirement) dated Apr. 23, 2010, U.S. Appl. No. 12/048,350, 9 pages.

Amendment and Response to Restriction Requirement dated May 25, 2010, U.S. Appl. No. 12/048,350, 7 pages.

Office Action dated Jul. 16, 2010, U.S. Appl. No. 12/048,350, 10 pages.

Amendment and Response to Office Action dated Jan. 8, 2011, U.S. Appl. No. 12/048,350, 11 pages.

Final Office Action dated Mar. 1, 2011, U.S. Appl. No. 12/048,350, 10 pages.

Notice of Appeal and Pre-Appeal Brief Request for Review dated Jul. 1, 2011, U.S. Appl. No. 12/048,350, 6 pages.

Decision on Pre-Appeal Brief Request for Review dated Aug. 12, 2011, U.S. Appl. No. 12/048,350, 2 pages.

Office Action dated Oct. 21, 2011, U.S. Appl. No. 12/048,350, 13 pages.

Amendment and Response to Office Action dated Jan. 23, 2012, U.S. Appl. No. 12/048,350, 14 pages.

Final Office Action dated Mar. 7, 2012, U.S. Appl. No. 12/048,350, 13 pages.

Notice of Appeal and Pre-Appeal Brief Requet for Review dated Jul. 9, 2012, U.S. Appl. No. 12/048,350, 7 pages.

Notice of Allowance and Fee(s) Due dated Aug. 28, 2012, U.S. Appl. No. 12/048,350, 8 pages.

UBIQUINOL AND ALPHA LIPOIC ACID COMPOSITIONS

CROSS-REFERENCE TO RELATED APPLICATION(S)

This application is a division of U.S. patent application Ser. No. 12/048,350, now U.S. Pat. No. 8,343,541 filed Mar. 14, 2008, entitled "Ubiquinol and Alpha Lipoic Acid Compositions," which claims benefit under 35 U.S.C. §119(e) to U.S. Serial Nos. 60/895,057, entitled "CoEnzyme Q-10 and Fatty Acid Compositions", filed Mar. 15, 2007 by Michael Fantuzzi, 60/908,477, entitled "Ubiquinol and Alpha Lipoic Acid Compositions", filed Mar. 28, 2007 by Michael Fantuzzi and 60/977,234, entitled "Ubiquinol and Alpha Lipoic Acid Compositions", filed Oct. 3, 2007 by Michael Fantuzzi, the contents of which are incorporated herein by reference in their entirety.

FIELD OF THE INVENTION

The present invention relates to the solubilization of coenzyme Q-10 and analogs thereof, at least one fatty acid and alpha lipoic acid, thereby providing coenzyme Q-10 in reduced form (ubiquinol).

BACKGROUND OF THE INVENTION

CoQ-10 (coenzyme Q-10) is a fat-soluble quinone that is structurally similar to vitamin K and commonly known as ubiquinone. CoQ-10 is found in most living organisms, and is essential for the production of cellular energy. CoQ-10 (2,3 dimethyl-5 methyl-6-decaprenyl benzoquinone) is an endogenous antioxidant found in small amounts in meats and seafood. Although CoQ-10 is found in all human cells, the highest concentrations of CoQ-10 occur in the heart, liver, kidneys, and pancreas. It is found naturally in the organs of many mammalian species.

CoQ-10 can be synthesized in the body or it can be derived from dietary sources. Situations may arise, however, when the need for CoQ-10 surpasses the body's ability to synthesize it. CoQ-10 can be absorbed by oral supplementation as evidenced by significant increases in serum CoQ-10 levels after supplementation.

CoQ-10 is an important nutrient because it lies within the membrane of a cell organelle called the mitochondria. Mitochondria are known as the "power house" of the cell because of their ability to produce cellular energy, or ATP, by shuttling protons derived from nutrient breakdown through the process of aerobic (oxygen) metabolism. CoQ-10 also has a secondary role as an antioxidant. CoQ-10, due to the involvement in ATP synthesis, affects the function of almost all cells in the body, making it essential for the health of all human tissues and organs. CoQ-10 particularly effects the cells that are the most metabolically active: heart, immune system, gingiva, and gastric mucosa Several clinical trials have shown CoQ-10 to be effective in supporting blood pressure and cholesterol levels. Furthermore, CoQ-10 has also been shown to improve cardiovascular health. CoQ-10 has been implicated as being an essential component in thwarting various diseases such as certain types of cancers. These facts lead many to believe that CoQ-10 supplementation is vital to an individual's well being.

CoQ-10 is sparingly soluble in most hydrophilic solvents such as water. Therefore, CoQ-10 is often administered in a powdered form, as in a tablet or as a suspension. However, delivery of CoQ-10 by these methods limits the bioavailability of the material to the individual.

Reduced benzoquinones in general, including reduced CoQ-10, are effective reducing agents for oxygen or lipid radicals. Reduced CoQ-10 appears to function as part of a complex chain of antioxidant activity. CoQ-10 helps facilitated reduction of radicals of alpha-tocopherol and ascorbate formed when these antioxidants are oxidized by oxygen or carboxyl radicals. There are no known enzymes for direct reduction of the tocopheryl radical or external ascorbate radical, but there are enzymes in all membranes which can reduce CoQ-10 and the reduced CoQ-10 can reduce the tocopheryl or ascorbate radicals to restore tocopherol or ascorbate.

CoQ-10 in endo membranes or plasma membranes is extensively in the reduced form, most of the CoQ-10 in total rat and human tissue is in the reduced form and most of the CoQ-10 in serum is in the reduced state.

There is a need in the art for an improved methodology to deliver increased amounts of bioavailable CoQ-10 to an individual in need thereof.

BRIEF SUMMARY OF THE INVENTION

The present invention pertains to the surprising discovery that ubiquinone (CoQ-10) is reduced in the presence of lipoic acid, optionally, in combination with one or more fatty acid(s) and, optionally, in combination with a monoterpene such as limonene. Furthermore, the reduced form of CoQ-10 (ubiquinol) is stable in the presence of alpha lipoic acid, optionally, with one or more fatty acids and, optionally, in combination with a monoterpene such as limonene.

In one aspect, the present invention provides compositions of ubiquinol in combination with a fatty acid. In another aspect, the present invention provides ubiquinol in combination with alpha lipoic acid in a sufficient amount such that the ubiquinol remains in the reduced form (ubiquinol) and does not significantly oxidize to ubiquinone. In yet another aspect, the present invention provides ubiquinol in combination with alpha lipoic acid in a sufficient amount such that the ubiquinol remains in the reduced form (ubiquinol) and does not oxidize to ubiquinone in combination with one or more fatty acids. In still another aspect, the present invention provides ubiquinol in combination with alpha lipoic acid in a sufficient amount such that the ubiquinol remains in the reduced form (ubiquinol) and does not oxidize to ubiquinone in combination with a monoterpene, such as limonene. In another aspect, the present invention provides ubiquinol in combination with alpha lipoic acid in a sufficient amount such that the ubiquinol remains in the reduced form (ubiquinol) and does not oxidize to ubiquinone in combination with a monoterpene, such as limonene, and one or more fatty acid(s).

The compositions of the invention are useful as dietary supplements or as nutraceuticals.

In particular, the compositions of the invention noted throughout the application are included in a soft gelatin (soft gel) capsule. Typically, the soft gelatin capsule encapsulates at least 5% by weight of the reduced CoQ-10 (from the combination of alpha lipoic acid, optionally a fatty acid(s) and CoQ-10, or ubiquinol in the presence of alpha lipoic acid, optionally in combination with a fatty acid) that can optionally be solubilized in at least one monoterpene. Typical monoterpenes include, for example, limonene, perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

In another embodiment, the present invention pertains to methods for delivery of an effective amount of bioavailable reduced CoQ-10 and/or CoQ-10, to an individual. The method includes providing reduced CoQ-10 and/or CoQ-10 provided by the compositions of present invention, such that an effective amount of reduced CoQ-10 and/or CoQ-10 is provided to the individual.

In still another embodiment, the present invention also includes packaged formulations of the invention and instructions for use of the tablet, capsule, elixir, etc.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention pertains to the surprising discovery that ubiquinone (CoQ-10) is reduced to reduced CoQ-10 (ubiquinol) in the presence of lipoic acid (e.g., alpha lipoic acid). Ideally, there is at least a molar equivalent of each of alpha lipoic acid and CoQ-10, so that the CoQ-10 is reduced to at least 95% or greater, e.g., 99 to 100%. In particular, a molar excess of alpha lipoic acid is used to help reduce the CoQ-10 to essentially only ubiquinol. In one aspect, one or more fatty acid(s) are included in the compositions. In another aspect, a monoterpene, such as limonene, is included with either the CoQ-10/alpha lipoic acid combination, optionally with one or more fatty acids, or ubiquinol is simply dissolved in the monoterpene, such as limonene, with or without a fatty acid and in the presence of alpha lipoic acid.

In another embodiment, the compositions include ubiquinol that is already reduced and is maintained with a sufficient quantity of alpha lipoic acid to help prevent oxidation of the ubiquinol back to the oxidized form of the ubiquinone. Again, the composition can include, optionally, either one or more fatty acid(s), a monoterpene such as limonene, or both.

The term "coenzyme Q" or "ubiquinone" is used throughout the present specification to describe a group of lipid soluble benzoquinones involved in electron transport in mitochondrial preparations, i.e., in the oxidation of succinate or reduced nicotine adenine dinucleotide (NADH) via the cytochrome system. The compounds can be described as: coenzyme $Q_n$ where n is 1 through 12 or ubiquinone (x) in which x designates the total number of carbon atoms in the side chain and can be any multiple of 5. Differences in properties are due to the difference in the chain length.

In one embodiment of the invention, the reduced form of coenzyme Q-10 is termed "ubiquinol". It should be understood that throughout the present specification that reference to coenzyme Q-10, CoQ-10, CoQ and ubiquinone all refer to this group of benzoquinones (where n is 1 through 12) and the terms are used interchangeably.

The term "ubiquinol" is used throughout the specification to describe the reduced form of coenzyme Q which is used as the active ubiquinone in compositions according to the present invention. In ubiquinol, the quinone ring of coenzyme Q is reduced such that the structure of the compound appears as set forth below. In ubiquinol, n in one embodiment is 10 and is derived from coenzyme Q-10. The amount of ubiquinol which is included in compositions according to the present invention ranges from about 0.1% to about 50% by weight of the final composition which can be encapsulated in a soft gelatin capsule, more particularly about 0.5% to about 10% by weight, even more particularly about 1% to about 5% by weight.

It should be understood that throughout the present specification that reference to reduced coenzyme Q-10, reduced CoQ-10, reduced CoQ and ubiquinol all refer to this group of reduced benzoquinones (where n is 1 through 12) and the terms are used interchangeably.

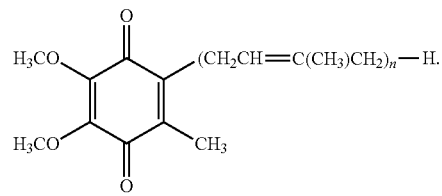

Ubiquinone (n = 10, Coensyme Q-10)

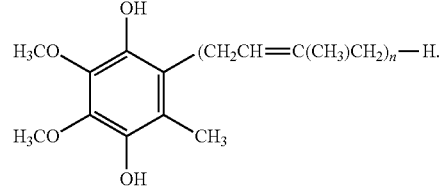

Ubiquinol (where n = 10 from the parent benzoquinone)

A commercial source of ubiquinol is QH™, Kaneka Corporation, Functional Foods Development Division, 3-2; 1-, Nakanoshima, Kita-Ku, Osaka 530-8288, Japan.

CoQ-10 is found in most living organisms, and is essential for the production of cellular energy. Ubiquinone is a naturally occurring hydrogen carrier in the respiratory chain (coenzyme Q) and structurally, it is a 2,3-dimethoxy-5-methyl-1,4-benzoquinone with a multiprenyl side chain, the number of isoprene units varying depending upon the organism from which it is derived. CoQ-10 analogs include reduced and semi-reduced CoQ-10 and ubiquinone derivatives described, for example, in WO 8803015, the teachings of which are incorporated herein by reference.

Semi-reduced ubiquinone, by analogy, can be depicted as a radical species (CoH.):

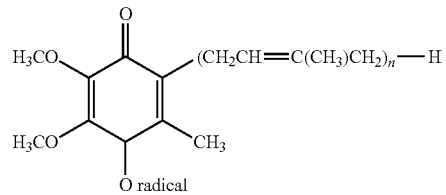

wherein n is as described above.

In certain embodiments, the CoQ is reduced in the presence of lipoic acid and, optionally, at least one fatty acid to provide a composition that includes at least about 50% reduced CoQ, more particularly, at least about 75% reduced CoQ, even more particularly, at least about 95%, 97%, 99%, 99.5% reduced CoQ based on a weight basis of the original weight of oxidized CoQ. In certain aspects, the oxidized form of CoQ cannot be detected when in the presence of an effective amount of lipoic acid and, optionally, a fatty acid and, optionally, a monoterpene. Typically, an effective amount of lipoic acid is at least a molar equivalent of lipoic acid to the oxidized CoQ. In instances where ubiquinol is the sole component, then alpha lipoic acid can be used to maintain the ubiquinol in a reduced state. Thus, the invention provides reduced CoQ compositions that are stable to oxidation.

The terms "lipoic acid" and "alpha lipoic acid" are used interchangeably herein and both refer to 1,2-dithione-3-pentanoic acid, also known as thioctic acid.

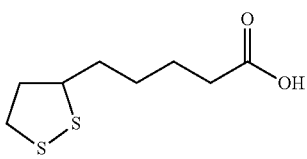

Thioctic acid (lipoic acid)

Lipoic acid exists as two enantiomers: the R-enantiomer and the S-enantiomers. Naturally-occurring lipoic acid occurs in the R-form, but synthetic lipoic acid (commonly known as alpha lipoic acid) is a racemic mixture of R-form and S-form. It should be understood that throughout the application, reference to lipoic acid therefore includes the R-enantiomer, the S-enantiomer, and the racemic mixture of R/S enantiomers.

The phrase "fatty acid," as used herein means an organic compound composed of unsubstituted alkyl or alkenyl groups containing 4 to 22 carbon atoms and characterized by a terminal carboxylic acid group.

Useful fatty acids include butyric acid (butanoic acid) caproic acid (hexanoic acid), caprylic acid (octanoic acid), capric acid (decanoic acid), caproleic acid (dec-9-enoic acid), lauric acid (dodecanoic acid), lauroleic acid (cis-5-lauroleic), myristic acid (tetradecanoic acid), myristoleic acid (cis-9-tetradecenoic), palmitic acid (hexadecanoic acid), palmitoleic acid (9-hexadecenoic acid), stearic acid (octadecanoic acid), oleic acid (9-octadecenoic acid), ricinoleic acid (12-hydroxy-9-octadecenoic acid), vaccenic acid (11-octadecenoic acid), valeric acid (pentanoic acid), linoleic acid (9,12-octadecadienoic acid), alpha-linolenic acid ((ALA) 9,12,15-octadecatrienoic acid), gamma-linolenic acid ((GLA) 6,9,12-octadecatrienoic acid), arachadonic acid (eicosanoic acid), gadoleic acid (9-eicosenoic acid), arachidonic acid ((AA) 5,8,11,14-eicosatetraenoic acid), EPA (5,8,11,14,17-eicosapentaenoic acid), behenic acid (docosanoic acid), erucic acid (13-docosenoic acid), DHA (4,7,10,13,16,19-docosahexaenoic), pelargonic acid (nonanoic acid), steridonic acid (6Z,9Z,12Z,15Z)-6,9,12,15-octadecatetraenoic acid) and lignoceric acid (tetracosanoic acid). In one aspect, the fatty acid is considered a carrier and dissolves the ingredients within the soft gelatin capsule. Suitable ingredients include ALA and ubiquinol and/or ubiquinone.

In one aspect, the lipoic acid 25% (weight lipoic acid/weight fatty acid(s)) (i.e., alpha-lipoic acid) is first dissolved in a mixture of two fatty acids, capric and caprylic acids at an elevated temperature of between about 25° C. and about 35° C. in, for example, a 3:7 ratio of the fatty acids. In one embodiment, the lipoic acid/fatty acid mixture is then dissolved in a monoterpene, such as limonene.

The encapsulation mixtures of the invention (mixtures of ubiquinone/ubiquinol with or without a monoterpene, and/or one or more fatty acids) result in encapsulation solutions that are crystal free. This is one unique aspect of the present invention that is believed to provide enhanced bioavailability of active agents to the individual in need thereof.

Therefore, it is possible to prepare encapsulation solutions of ubiquinone/ALA/monoterpene, ubiquinol/ALA/monoterpene, ubiquinone/ALA/fatty acid(s), ubiquinol/ALA/fatty acid(s), ubiquinone/ALA/monoterpene/fatty(acid) or ubiquinol/ALA/monoterpene/fatty acid(s) suitable for encapsulation within a soft gelatin capsule. In one aspect, the monoterpene is limonene. In another aspect, the encapsulation solution is free of solids, such as crystallization of the active agent(s), such as ALA, ubiquinol or ubiquinone.

L-carnitine is recognized in the art and facilitates transport of materials through the mitochondrial membrane. L-carnitine is an essential fatty acid metabolism cofactor that helps to move fatty acids to the mitochondria from the cytoplasm. This is an important factor as this is where CoQ-10 uptake occurs.

In one aspect of the present invention, L-carnitine is included in soft gel formulations in combination with CoQ-10. Suitable ratios of L-carnitine and CoQ-10 are known in the art and include those described in U.S. Pat. No. 4,599,232, issued to Sigma Tau Industrie Faramaceutiche Riunite S.p.A. on Jul. 8, 1986, the teachings of which are incorporated herein in their entirety. In particular, combinations of limonene, CoQ-10 and L-carnitine in soft gel formulations are of importance. The present invention provides the advantage of solvating large amounts (relative to that of current state of the art) of CoQ-10 in limonene in a soft gel capsule along with an additive, such as L-carnitine.

It should be understood, that throughout the specification, reference is made to CoQ-10 or amino acids, such as carnitine, and that such reference includes the analogs thereof.

The term "amino acid" as used herein includes, but is not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids and analogs thereof.

For example amino acid analogs, such as carnitine "analogs" include acetylated products, fumarate derivatives and the like, and acceptable ammonium and metal salts thereof.

The term "carnitine" is also known as 3-Carboxy-2-hydroxy-N,N,N-trimethyl-1-propanaminium hydroxide, inner salt; (3-carboxy-2-hydroxypropyl)trimethylammonium hydroxide, inner salt; gamma-amino-beta-hydroxybutyric acid trimethylbetaine; gamma-trimethyl-beta-hydroxybutyrobetaine; 3-hydroxy-4-(trimethyl-ammonio)butanoate. See The Merck Index (1989), p. 281 and references cited therein. Therefore, "carnitine" and "carnitine analogs" includes, but is not limited to racemic or essentially pure L-carnitine (carnitine), or a corresponding alkanoyl-carnitine such as e.g. acetyl-carnitine or propionyl-carnitine, or a suitable salt of such compounds such as e.g. L-carnitine tartrate, L-carnitine fumarate, L-carnitine-magnesium-citrate, acetyl-L-carnitine tartrate, acetyl-L-carnitine-magnesium-citrate, or any mixture of the afore mentioned compounds.

Carnitine and carnitine analogs also include those described in U.S. Pat. Nos. 5,362,753, 4,687,782, 5,030,458, 5,030,657, 4,343,816, 5,560,928, 5,504,072, 5,391,550 and 5,240,961, the teachings of which are incorporated herein by reference in their entirety.

The phrase "sufficient quantity" of a given material, such as a monoterpene, "suitable to solubilize" is therefore intended to mean that that amount of a material, such as a monoterpene or a carrier (e.g., a fatty acid) that will dissolve a component under a given set of conditions, generally, those at ambient temperature. This determination should be understood by one skilled in the art and can be determined by methods known in the art, such as by solubility studies.

One of the particular advantages of utilizing the combination of ubiquinol and/or CoQ with lipoic acid, optionally in molar excess, optionally, one or more fatty acids, and optionally a monoterpene, is the ability to prevent oxidation of the ubiquinol back to the corresponding ubiquinone. Not to be limited by theory, it is believed that once an individual ingests the formulation of the invention, that the ubiquinol is then more bioavailable to the individual than the equivalent oxidized CoQ-10, and thus is better absorbed.

In one aspect, the present invention provides a molar ratio of lipoic acid to ubiquinol in the range of from about 0.1:1 to about 2.5:1 to ensure that the ubiquinol remains reduced. Suitable molar ratio ranges include from about 0.2:1 to about 2.3:1, from about 0.4:1 to about 1.6:1 and in particular about 0.9:1 to about 1.1:1.

Use of the lipoic acid in combination with the ubiquinol and/or coenzyme Q provides that the ubiquinol remains unoxidized for at least about 30 days at ambient temperature, more particularly at least about 120 days at ambient temperature and even more particularly at least about 365 days, even more particularly at least about 2 years or longer at ambient temperature, wherein at least about 85 to about 95% of the original amount of ubiquinol remains unoxidized. In particular, at least about 85%, 86%, 87% and so forth up to about 100% (e.g., 99.9%) of ubiquinol in the sample remains unoxidized (or any remaining ubiquinone is reduced to ubiquinol) over the given time frames.

A major advantage of utilizing lipoic acid with the ubiquinol and/or ubiquinone is in the processing/manufacturing stages. It has been surprisingly found that the lipoic acid helps stabilize the ubiquinol. A stable formulation of ubiquinol is much easier to handle, store and work with because ubiquinol by itself is very easily oxidized and as such, requires very careful precise handling. Special precautions normally need to be taken to make sure that no air/light, temperature changes take place during the processing and manufacturing with the material. With the present invention, the material (incorporating lipoic acid) can be handled just like any fill material and no special handling, processing or storage of the formulations is needed. This is a huge advantage to the manufacturer, especially since ubiquinol is very expensive and degrading it even a little can be very costly.

In the specification and in the claims, the terms "including" and "comprising" are open-ended terms and should be interpreted to mean "including, but not limited to . . . ." These terms encompass the more restrictive terms "consisting essentially of" and "consisting of.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art.

Nothing herein is to be construed as an admission that the invention is not entitled to antedate such disclosure by virtue of prior invention.

The term "monoterpene" as used herein, refers to a compound having a 10-carbon skeleton with non-linear branches. A monoterpene refers to a compound with two isoprene units connected in a head-to-end manner. The term "monoterpene" is also intended to include "monoterpenoid", which refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth.

It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein.

Suitable examples of monoterpenes include, but are not limited to, limonene, pinene, cintronellol, terpinene, nerol, menthane, carveol, S-linalool, safrol, cinnamic acid, apiol, geraniol, thymol, citral, carvone, camphor, etc. and derivatives thereof. For information about the structure and synthesis of terpenes, including terpenes of the invention, see Kirk-Othmer Encyclopedia of Chemical Technology, Mark, et al., eds., 22:709-762 3d Ed (1983), the teachings of which are incorporated herein in their entirety.

In particular, suitable limonene derivatives include perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

Formulation of one or more of the following: CoQ, ubiquinol, lipoic acid, fatty acid(s) and, optionally, additional components, can be accomplished by many methods known in the art. For example, the ubiquinol, lipoic acid, fatty acid composition can be formulated in a suspension, an emulsion, an elixir, a solution, a caplet that harbors the liquid, or in a soft gelatin capsule (that harbors the liquid). Often the formulation will include an acceptable carrier, such as oil, or other suspending agent.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carriers, beeswax can be used as a suitable carrier, as well as suspending agents such as silica (silicon dioxide).

The formulations of the invention are considered dietary supplements useful to the increase the amounts of CoQ and/or optional nutritive ingredients in individuals in need thereof.

Alternatively, the formulations of the invention are also considered to be nutraceuticals. The term "nutraceutical" is recognized in the art and is intended to describe specific chemical compounds found in foods that may prevent disease. CoQ-10 and amino acids are such compounds.

The formulations of the invention can further include various ingredients to help stabilize, or help promote the bioavailability of the CoQ and/or amino acid(s), or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition of the invention in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the composition of the invention in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present compositions. Optional additives of the present composition include, without limitation, phospholipids, L-carnitine, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as carnosol, carnosic acid and rosmanol found in rosemary and hawthorn extract, proanthocyanidins such as those found in grapeseed or pine bark extract, and green tea extract.

The term "flavonoid" as used herein is recognized in the art and is intended to include those plant pigments found in many foods that are thought to help protect the body from cancer. These include, for example, epi-gallo catechin gallate (EGCG), epi-gallo catechin (EGC) and epi-catechin (EC).

Any dosage forms, and combinations thereof, are contemplated by the present invention. Examples of such dosage forms include, without limitation, chewable tablets, elixirs, liquids, solutions, suspensions, emulsions, capsules, soft gelatin capsules, hard gelatin capsules, caplets, lozenges, chewable lozenges, suppositories, creams, topicals, ingestibles, injectables, infusions, health bars, confections, animal feeds, cereals, cereal coatings, and combinations thereof. The preparation of the above dosage forms are well known to persons of ordinary skill in the art.

For example, health bars can be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules can be prepared, for example, without limitation, by dispersing the formulation in an appropriate vehicle (e.g. rice bran oil, monoterpene, fatty acid(s) and/or beeswax or combinations thereof) to form a high viscosity mixture. This mixture is then encapsulated with a gelatin based film using technology and machinery known to those in the soft gel industry. The industrial units so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally limonene, in combination with rice bran oil and/or beeswax if desired) and can include, apart form the antioxidant actives, a hydrophilic matrix. The hydrophilic matrix, if present, is a polyethylene glycol having an average molecular weight of from about 200 to 1000. Further ingredients are optionally thickening agents. In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes is mature technologies and are all widely available to any one wishing to prepare soft gelatin capsules.

Typically, when a soft gel capsule is prepared, the total weight is between about 250 milligrams and about 2.5 gram in weight, e.g., 400-750 milligrams. Therefore, the total weight of additives, such as vitamins and antioxidants, is between about 80 milligrams and about 2000 milligrams, alternatively, between about 100 milligrams and about 1500 milligrams, and in particular between about 120 milligrams and about 1200 milligrams. In particular, the soft gel capsule typically weighs between about 1000 milligrams and 1300 milligrams, wherein the percentage fill is about 50% of the entire weight of the capsule, i.e., from about 500 to about 650 milligrams fill weight. The fill weight includes the active ingredient(s), solubilizing agents, etc.

Preparation of the soft gel capsules was accomplished by methods well known in the art including, but not limited to those described throughout the specification and in U.S. Pat. Nos. 6,616,942, 6,623,734 and pending U.S. Ser. Nos. 10/035,753 and 09/825,920, the contents of which are incorporated herein by reference in their entirety.

For example, a soft gel capsule can be prepared by mixing alpha lipoic acid with ubiquinol and/or CoQ-10 with one or more fatty acids until dissolution occurs. To the solution can then be added a carrier, such as a monoterpene, e.g., limonene. The solution is then encapsulated within a gelatin capsule as described above.

The present invention also provides packaged formulations and instructions for use of the tablet, capsule, elixir, etc. Typically, the packaged formulation, in whatever form, is administered to an individual in need thereof that requires an increase in the amount of reduced or oxidized CoQ in the individual's diet. Typically, the dosage requirement is between about 1 to about 4 dosages a day.

CoQ-10 has been implicated in various biochemical pathways and is suitable for the treatment of cardiovascular conditions, such as those associated with, for example, statin drugs that effect the body's ability to product CoQ-10 naturally. CoQ-10 has also been implicated in various periodontal diseases. Furthermore, CoQ-10 has been implicated in mitochondrial related diseases and disorders, such as the inability to produce acetyl coenzyme A, neurological disorders, for example, such as Parkinson's disease and, Prater-Willey syndrome.

The following paragraphs enumerated consecutively from 1 through 33 provide for various aspects of the present invention. In one embodiment, in a first paragraph (1), the present invention provides a soft gelatin capsule, comprising an encapsulated solution comprising a ubiquinol; a sufficient quantity of lipoic acid to maintain the ubiquinol in its reduced form; and one or more fatty acids, such that the ubiquinol comprises about 95% by weight of a total amount of ubiquinol and coenzyme Q in the solution.

2. The soft gelatin capsule of paragraph 1, wherein the ubiquinol content is about 98% by weight of the total weight of ubiquinol and coenzyme Q in the solution.

3. The soft gelatin capsule of paragraph 2, wherein the ubiquinol content is about 99% by weight of the total weight of ubiquinol and coenzyme Q in the solution.

4. The soft gelatin capsule of any of paragraphs 1 through 3, wherein the molar ratio of lipoic acid to ubiquinol is from about 0.1:1 to about 2.5:1.

5. The soft gelatin capsule of any of paragraphs 1 through 4, wherein the fatty acid is butanoic acid, hexanoic acid, octanoic acid, decanoic acid, dodecanoic acid, tetradecanoic acid, hexadecanoic acid, 9-hexadecenoic acid, octadecanoic acid, 9-octadecenoic acid, 12-hydroxy-9-octadecenoic acid, 11-octadecenoic acid, 9,12-octadecadienoic acid, 9,12,15-octadecatrienoic acid, 6,9,12-octadecatrienoic acid, eicosanoic acid, 9-eicosenoic acid, 5,8,11,14-eicosatetraenoic acid, 5,8,11,14,17-eicosapentaenoic acid, docosanoic acid, 13-docosenoic acid, 4,7,10,13,16,19-docosahexaenoic, tetracosanoic acid or mixtures thereof.

6. The soft gelatin capsule of paragraph 5, wherein the fatty acid is a combination of decanoic acid and octanoic acid.

7. The soft gelatin capsule of paragraph 6, wherein the ratio of decanoic acid to octanoic acid is 3:7.

8. The soft gelatin capsule of any of paragraphs 1 through 7, further comprising a monoterpene.

9. The soft gelatin capsule of paragraph 8, wherein the monoterpene is limonene or a derivative thereof.

10. The soft gelatin capsule of paragraph 9, wherein the limonene derivative is perillyl alcohol, perillic acid, cis-dihydroperillic acid, trans-dihydroperillic acid, methyl esters of perillic acid, methyl esters of dihydroperillic acid, limonene-2-diol, uroterpenol, or a combination thereof.

11. The soft gelatin capsule of any of paragraphs 1 through 10, wherein the encapsulated ubiquinol solution is stable to oxidation for at least about 30 days, such that about 95% ubiquinol remains from the original total amount of ubiquinol and coenzyme Q in the solution.

12. The soft gelatin capsule of any of paragraphs 1 through 11, wherein the encapsulated ubiquinol solution is stable to oxidation for at least about 120 days, such that about 95% ubiquinol remains from the original total amount of ubiquinol and coenzyme Q in the solution.

13. The soft gelatin capsule of any of paragraphs 1 through 12, wherein the encapsulated ubiquinol solution is stable to oxidation for at least about 365 days, such that about 95% ubiquinol remains from the original total amount of ubiquinol and coenzyme Q in the solution.

14. A method for the delivery of an effective amount of ubiquinol to an individual in need thereof, comprising the steps of providing a soft gelatin capsule as in paragraph 1, such that an effective amount of ubiquinol is provided to an individual.

15. A packaged nutraceutical formulation comprising:
a soft gelatin capsule as in paragraph 1 and
instructions for use thereof.

16. A method to prevent oxidation of a ubiquinol to a ubiquinone or a semi-ubiquinone, comprising the step of:
contacting a sufficient amount of alpha lipoic acid with ubiquinol, such that oxidation of the ubiquinol to a ubiquinone or a semi-ubiquinone does not occur.

17. A soft gelatin capsule, comprising an encapsulated solution comprising:
a ubiquinol;
a sufficient quantity of lipoic acid to maintain the ubiquinol in its reduced form; and a monoterpene, such that the ubiquinol comprises about 95% by weight of a total amount of ubiquinol and coenzyme Q in the solution.

18. The soft gelatin capsule of paragraph 17, wherein the ubiquinol content is about 98% by weight of the total weight of ubiquinol and coenzyme Q in the solution.

19. The soft gelatin capsule of paragraph 18, wherein the ubiquinol content is about 99% by weight of the total weight of ubiquinol and coenzyme Q in the solution.

20. The soft gelatin capsule of paragraph 17, wherein the ratio of lipoic acid to ubiquinol is from about 0.1:1 to about 2.5:1.

21. The soft gelatin capsule of paragraph 17, wherein the monoterpene is limonene or a derivative thereof.

22. The soft gelatin capsule of paragraph 21, wherein the limonene derivative is perillyl alcohol, perillic acid, cis-dihydroperillic acid, trans-dihydroperillic acid, methyl esters of perillic acid, methyl esters of dihydroperillic acid, limonene-2-diol, uroterpenol, or a combination thereof.

23. The soft gelatin capsule of paragraph 17, wherein the encapsulated ubiquinol solution is stable to oxidation for at least about 30 days, such that about 95% ubiquinol remains from the original total amount of ubiquinol and coenzyme Q in the solution.

24. The soft gelatin capsule of paragraph 17, wherein the encapsulated ubiquinol solution is stable to oxidation for at least about 120 days, such that about 95% ubiquinol remains from the original total amount of ubiquinol and coenzyme Q in the solution.

25. The soft gelatin capsule of paragraph 17, wherein the encapsulated ubiquinol solution is stable to oxidation for at least about 365 days, such that about 95% ubiquinol remains from the original total amount of ubiquinol and coenzyme Q in the solution.

26. A method for the delivery of an effective amount of ubiquinol to an individual in need thereof, comprising the steps of
providing a soft gelatin capsule as in paragraph 17, such that an effective amount of ubiquinol is provided to an individual.

27. A packaged nutraceutical formulation comprising:
a soft gelatin capsule as in paragraph 1 and
instructions for use thereof.

28. The method of paragraph 16, wherein the percentage of the ubiquinol to the oxidized ubiquinone or the semi-ubiquinone on a weight basis is at least 95%.

29. The method of paragraph 16, wherein the percentage of the ubiquinol to oxidized ubiquinone or the semi-ubiquinone on a weight basis is at least 98%.

30. The method of any of paragraphs 16, 28 or 29, wherein the ubiquinol remains reduced for at least about 30 days.

31. The method of any of paragraphs 16, 28 or 29, wherein the ubiquinol remains reduced for at least about 120 days.

32. The method of any of paragraphs 16, 28 or 29, wherein the ubiquinol remains reduced for at least about 365 days.

33. The method of any of paragraphs 16 or 28 through 32, wherein the molar ratio of lipoic acid to ubiquinol is from about 0.1:1 to about 2.5:1.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Ubiquinol (QH™, Kaneka Corporation, Functional Foods Development Division, 3-2; 1-, Nakanoshima, Kita-Ku, Osaka 530-8288, Japan) formulation trial #1:

QH™ working solution (ws): 20.0 g QH™ was mixed in 60.0 g D-Limonene (LI-FA-MX-00454) at ~30° C. until completely dissolved. The beaker was nitrogen-blanketed and put aside for mixing the trial formulations.

Alpha-Lipoic Acid (ALA) working solution (ws): A 25% (w/w)(weight/weight) ALA solution was prepared with 7:3 caprylic acid: capric acid at ~30° C. until completely dissolved.

The following trial mixes were prepared:

Trial mix #1 (100 mg QH™/400 mg): 8.0 g of the QH™ working solution were placed into a small glass vial, nitrogen blanketed and labeled: 100 mg QH™/400 mg.

Trial mix #2 (100 mg QH™/425 mg): 7.53 g of the QH™ ws and 0.47 g of the ALA ws were mixed, placed into a small vial, nitrogen blanketed and labeled: 100 mg QH™/425 mg.

Trial mix #3 (100 mg QH™/450 mg): 7.11 g QH™ ws and 0.89 g ALA ws were mixed, placed into a small vial, nitrogen blanketed and labeled: 100 mg QH™/450 mg.

Trial mix #4 (100 mg QH™/500 mg): 6.40 g QH™ ws and 1.60 g ALA ws were mixed, placed into a small vial, nitrogen blanketed and labeled: 100 mg QH™/500 mg.

trial mix #5 (100 mg QH™/650 mg): 4.92 g QH™ ws and 3.08 g ALA ws were mixed, placed in a small vial, nitrogen blanketed and labeled: 100 mg QH™/650 mg.

Trial mix #6 (100 mg QH™/900 mg): 3.56 g QH™ ws and 4.44 g ALA ws were mixed, placed into a small vial, nitrogen blanketed and labeled: 100 mg QH™/900 mg.

Trial mix #7 (100 mg QH™/1000 mg): 3.20 g QH™ ws and 4.80 g ALA ws were mixed, placed into a small vial, nitrogen blanketed and labeled: 100 mg QH™/1000 mg.

Trial mix #8 (100 mg QH™/1250 mg): 2.56 g QH™ ws and 5.44 g ALA ws were mixed, placed into a small vial, nitrogen blanketed and labeled: 100 mg QH™/1250 mg.

Trial mix #9 (100 mg QH™/1500 mg): 2.13 g QH™ ws and 5.87 g ALA ws were mixed, placed into a small vial, nitrogen blanketed and labeled: 100 mg QH™/1500 mg.

The remainder of QH™ working solution was placed into large amber glass vials, nitrogen blanketed and labeled: QH™ working solution 25%, dated and place into refrigerator.

100 in the trials represents 100 mg ubiquinol/CoQ10 per dosage formula, and the denominator is for the total fill weight for each dosage. Each formulation is for 100 mg/ubiquinol/CoQ10 per dosage. A standard amount of ubiquinol/CoQ10 was maintained, adding increasing amounts of ALA solution, to determine an optimal amount/range for reduction of oxidation. To keep the potencies at 100 mg/dosage, the fill weights were increased as the ALA was increased; hence the 100 mg CoQ10/increasing formula fill weights.

The vials were stored at ambient temperature. Samples were removed over time and analyzed for ubiquinol and for CoQ10 (oxidized form) via HPLC. Knowing how much ubiquinol/CoQ10 was present in each sample, a determination was made regarding the amount of CoQ10 or ubiquinol assayed from the total and a determination regarding oxidation was made. The table below shows the amount of ubiquinol remaining after 36 days at room temperature.

| Sample #: | Fill Weight (mg): | moles QH: | moles ALA: | QH:ALA (moles) | % QH remaining after 36 days |
|---|---|---|---|---|---|
| 1 | 400 | 0.26 | 0 | 0 | 65 |
| 2 | 425 | 0.26 | 0.0303 | 1:0.117 | 100 |
| 3 | 450 | 0.26 | 0.0606 | 1:0.233 | 93 |
| 4 | 500 | 0.26 | 0.1212 | 1:0.466 | 95 |
| 5 | 650 | 0.26 | 0.3032 | 1:1.660 | 96 |
| 6 | 900 | 0.26 | 0.6052 | 1:2.328 | 93 |
| 7 | 1000 | 0.26 | 0.7270 | 1:2.796 | Not reliable |
| 8 | 1250 | 0.26 | 1.2218 | 1:4.699 | Not reliable |
| 9 | 1500 | 0.26 | 1.333 | 1:5.128 | Not reliable | variance of amount of % QH remaining ± 2%

Soft gelatin capsules encapsulating ubiquinol/CoQ10 or mixtures thereof with a fatty acid mixture and alpha-lipoic acid can be prepared by the following general procedure. Caprylic acid and capric acid are poured into a blending machine and stirred until clear and completely liquid. The liquid can then be heated and alpha lipoic acid is added and mixed until completely dissolved. This solution is the set aside.

D-limonene is added to a blending machine and gently warmed to about 30° C.

Ubiquinol (or CoQ-10 or mixtures thereof) is added to D-limonene and stirred. Optionally, the ubiquinol is added directly to the liquid fatty acid/alpha lipoic acid solution without the use of D-limonene.

The alpha lipoic acid/capric acid/caprylic acid solution is added to the ubiquinol/D-limonene solution and mixed. Optionally, the ubiquinol is added directly to the liquid fatty acid/alpha lipoic acid solution without the use of D-limonene.

The solution is then filtered and encapsulated in soft gelatin capsules.

Exemplary Soft Gel Formulations

The following are general processes used to prepare soft gelatin capsules containing varying amounts of ubiquinol.

15.02 g of capric acid and 35.04 of caprylic acid (3:7) were mixed with 299.95 g D-limonene in a blending machine, under vacuum, at a temperature between about 23-30° C. until uniformly mixed and in a liquid state.

12.52 g alpha lipoic acid and 99.98 g ubiquinol (QH™) were added to the warmed mixture and mixed under vacuum at a temperature between about 23-30° C. until completely dissolved.

The resultant liquid mixture was encapsulated into a soft gelatin capsule using the procedures described above. The fill weight for each capsule was approximately 465 mg, giving a little over 100 mg ubiquinol per capsule.

Specific Formulations:

Caprylic acid and capric acid were poured into a blending machine and stirred until clear and completely liquid. The solution was heated to about 30° C. and alpha lipoic acid was added and stirred until completely dissolved. This solution was set aside until needed.

A blending machine was nitrogen blanketed, D-limonene was poured into it and heated to about 30° C. Ubiquinol was added to the D-limonene and stirred under vacuum for at least 20 minutes. The alpha lipoic acid/capric acid/caprylic acid was added to the ubiquinol/D-limonene solution, heated to about 30° C., then mixed under vacuum for at least 40 minutes.

The solution was then filtered, placed into a nitrogen blanketed receiver and sent for encapsulation.

CoQH-CF 50 mg:

| | |
|---|---|
| Ubiquinol (QH- Kaneka) | 53.1250 mg (98% material so an overage is used to make 50 mg) |
| Capric acid | 4.6850 mg |
| D-limonene 95% | 168.1250 mg |
| Alpha lipoic acid | 3.1250 mg |
| Caprylic acid | 10.9400 mg |
| Total capsule fill weight | 240.0000 mg |

CoQH-CF 100 mg:

| | |
|---|---|
| Ubiquinol (QH- Kaneka) | 106.2500 mg (98% material so an overage is used to make 100 mg) |
| Capric acid | 9.3700 mg |
| D-limonene | 336.2500 mg |
| Alpha lipoic acid | 6.2500 mg |
| Caprylic acid | 21.8800 mg |
| Total capsule fill weight | 480.0000 mg |

CoQH-CF 100 Mg (with Stability Testing Performed on Encapsulated Solution:

| | |
|---|---|
| Ubiquinol (QH-Keneka) | 104.13 mg |
| Alpha-lipoic acid | 6.25 mg |
| Capric acid | 9.37 mg |
| Caprylic acid | 21.88 mg |
| D-Limonene | 336.25 mg |
| Total capsule fill weight | 480.00 mg |

| Measurement at room temperature via HPLC | Time zero | 3 months | 6 months |
|---|---|---|---|
| Ubiquinol | 100-104%* | 104% | 102% |

*percentage over 100% as an overage of ubiquinol was used variance of amount of % QH remaining ± 2%

Samples were encapsulated in soft gelatin capsules as described above and stored at ambient temperature. Capsules were then sampled by opening the capsule and removing the solution for testing by HPLC.

Although the present invention has been described with reference to preferred embodiments, persons skilled in the art will recognize that changes may be made in form and detail without departing from the spirit and scope of the invention.

All literature and patent references cited throughout the application are incorporated by reference into the application for all purposes.

What is claimed is:

1. A method of reducing oxidation of an ubiquinol to a ubiquinone or a semi-ubiquinone, comprising the step of:
   contacting a sufficient amount of alpha lipoic acid with ubiquinol to form a solution;
   wherein a molar ratio of alpha lipoic acid to ubiquinol is from 0.1:1 to 0.4:1; and,
   thus reducing oxidation of the ubiquinol to a ubiquinone or a semi-ubiquinone.

2. The method of claim 1, wherein the ubiquinol content of the solution is about 95% by weight of the total weight of ubiquinol, ubiquinone, and semi-ubiquinone in the solution.

3. The method of claim 1, wherein the solution further comprises a fatty acid selected from the group consisting of butanoic acid, hexanoic acid, octanoic acid, decanoic acid, dodecanoic acid, tetradecanoic acid, hexadecanoic acid, 9-hexadecenoic acid, octadecanoic acid, 9-octadecenoic acid, 12-hydroxy-9-octadecenoic acid, 11-octadecenoic acid, 9,12-octadecadienoic acid, 9,12,15-octadecatrienoic acid, 6,9,12-octadecatrienoic acid, eicosanoic acid, 9-eicosenoic acid, 5,8,11,14-eicosatetraenoic acid, 5,8,11,14,17-eicosapentaenoic acid, docosanoic acid, 13-docosenoic acid, 4,7,10,13,16,19-docosahexaenoic, tetracosanoic acid or mixtures thereof.

4. The method of claim 3, wherein the fatty acid is a combination of decanoic acid and octanoic acid.

5. The method of claim 4, wherein decanoic acid to octanoic acid is present in a ratio of 3:7.

6. The method of claim 1, wherein the solution further comprises a monoterpene.

7. The method of claim 6, wherein the monoterpene is limonene or a derivative thereof.

8. The method of claim 7, wherein the limonene is d-limonene.

9. The method of claim 1, wherein the ubiquinol in the solution is stable to oxidation for about 30 days, such that about 95% ubiquinol remains from the original total amount of ubiquinol.

10. The method of claim 1, wherein the ubiquinol in the solution is stable to oxidation for about 120 days, such that about 95% ubiquinol remains from the original total amount of ubiquinol.

11. The method of claim 1, wherein the ubiquinol in the solution is stable to oxidation for about 365 days, such that about 95% ubiquinol remains from the original ubiquinol.

12. The method of claim 1, further comprising the step of:
encapsulating the solution containing alpha lipoic acid and ubiquinol in a soft gelatin capsule.

13. The method of claim 12, further comprising the steps of:
administering one or more soft gelatin capsules to an individual, such that an effective amount of ubiquinol is provided to the individual.

14. The method of claim 2, wherein the ubiquinol content is about 98% by weight of the total weight of ubiquinol, ubiquinone, and semi-ubiquinone in the solution.

15. The method of claim 14, wherein the ubiquinol content is about 99% by weight of the total weight of ubiquinol, ubiquinone, and semi-ubiquinone in the solution.

16. The method of claim 1, further comprising a fatty acid and a monoterpene.

17. The method of claim 16, wherein the fatty acid is decanoic acid, octanoic acid, or a combination thereof, and the monoterpene is limonene or a derivative thereof.

18. The method of claim 17, wherein the fatty acid is a combination of decanoic acid and octanoic acid, and the limonene is d-limonene.

* * * * *